(12) United States Patent
Straehnz et al.

(10) Patent No.: US 8,568,426 B2
(45) Date of Patent: Oct. 29, 2013

(54) LIGATION DEVICE AND METHOD

(75) Inventors: Jens-Peter Straehnz, Hamburg (DE); Burkhard Peters, Wattenbek (DE); Peter A. Meier, Hamburg (DE)

(73) Assignee: Ethicon, Inc., Somerville, NJ (US)

( * ) Notice: Subject to any disclaimer, the term of this patent is extended or adjusted under 35 U.S.C. 154(b) by 223 days.

(21) Appl. No.: 12/882,347

(22) Filed: Sep. 15, 2010

(65) Prior Publication Data

US 2012/0065654 A1    Mar. 15, 2012

(51) Int. Cl.
*A61B 17/10*    (2006.01)

(52) U.S. Cl.
USPC .......................................... 606/140; 606/157

(58) Field of Classification Search
USPC ......... 606/110, 112, 113, 139, 140, 144, 148, 606/151, 154, 157, 158; 227/901, 902; 29/235; 206/63.5; 128/843
See application file for complete search history.

(56) References Cited

U.S. PATENT DOCUMENTS

| | | | |
|---|---|---|---|
| 3,382,873 A | 5/1968 | Banich et al. | |
| 3,760,810 A | 9/1973 | Van Hoorn | |
| 4,368,736 A * | 1/1983 | Kaster | 606/153 |
| 4,548,201 A | 10/1985 | Yoon | |
| 4,860,746 A | 8/1989 | Yoon | |
| 5,158,563 A | 10/1992 | Cosman | |
| 5,203,863 A | 4/1993 | Bidoia | |
| 5,464,412 A | 11/1995 | Budding | |
| 5,578,047 A | 11/1996 | Taylor | |
| 5,713,920 A | 2/1998 | Bezwada et al. | |
| 5,741,273 A | 4/1998 | O'Regan | |
| 5,788,715 A | 8/1998 | Golden et al. | |
| 6,136,009 A | 10/2000 | Mears | |
| 6,613,060 B2 | 9/2003 | Adams et al. | |
| 7,118,528 B1 | 10/2006 | Piskun | |
| D538,428 S | 3/2007 | Andreen | |
| 7,578,828 B2 * | 8/2009 | Gittings et al. | 606/153 |
| 7,641,652 B2 | 1/2010 | Coe et al. | |
| 7,722,627 B2 | 5/2010 | Andreen | |
| 7,795,326 B2 | 9/2010 | Salamone et al. | |

(Continued)

FOREIGN PATENT DOCUMENTS

| | | |
|---|---|---|
| EP | 1155660 A | 12/2003 |
| EP | 1339330 A | 8/2007 |

(Continued)

OTHER PUBLICATIONS

Bronstein, M. et al., "Ligation under vision of haemorrhoidal cushions for therapy of bleeding haemorrhoids", Tech. Coloproctol. 12(2): 119-22 (2008).

(Continued)

*Primary Examiner* — Corrine M McDermott
*Assistant Examiner* — Robert Lynch

(57) ABSTRACT

A device and method for ligating diseased tissue. The device includes a flexible, substantially tubular sleeve adapted to be positioned around tissue to be ligated and having first and second ends, and at least one anchoring member coupled to the tubular sleeve having an anchoring element positioned substantially adjacent to the first end. The anchoring member has at least one projecting element extending therefrom and adapted to engage healthy tissue when the ligation device is positioned around the tissue to be ligated. The device further includes an elastic element positioned around the periphery of the sleeve and adapted to apply a constrictive force around the periphery of the sleeve.

13 Claims, 5 Drawing Sheets

(56) References Cited

U.S. PATENT DOCUMENTS

| | | | |
|---|---|---|---|
| 2002/0072757 A1* | 6/2002 | Ahmed et al. | 606/139 |
| 2002/0111639 A1 | 8/2002 | Armstrong | |
| 2004/0087955 A1 | 5/2004 | Bordi | |
| 2008/0033522 A1* | 2/2008 | Grewe et al. | 623/1.11 |
| 2009/0076595 A1* | 3/2009 | Lindquist et al. | 623/1.43 |
| 2009/0105728 A1 | 4/2009 | Noda et al. | |

FOREIGN PATENT DOCUMENTS

| | | |
|---|---|---|
| GB | 2010094 A | 6/1979 |
| JP | 2003144442 A | 5/2003 |
| WO | WO 2007102152 A2 | 9/2007 |

OTHER PUBLICATIONS

Diurni, M. et al. "Hemorrhoidectomy in day surgery", Int. J. Surg. 6 Suppl. 1:S53-5 (2008).

Hussain, J.N. "Haemorrhoids", Essentials of clinical management. Aust. Fam Physician 30(1): 29-35 (2001).

Shanmugam, V., et al. "Rubber band ligation versus excisional hemorrhoidectomy for hemorrhoids" Cochrane Database Syst Rev. (3): CD005034 (2005).

Tamelis, A, "Evidence based treatment of hemorrhoids" Acta Chir Iugosl. 55(3): 127-32 (2008).

International Search Report for International Application No. PCT/US2011/051337 dated Jan. 11, 2012.

* cited by examiner

LIGATION DEVICE AND METHOD

BACKGROUND OF THE INVENTION

1. Field of the Invention

The present invention relates generally to devices and methods for ligating tissue of a patient, and more particularly, to a device and method particularly suitable for ligating hemorrhoids or other regions of inverted tissue.

2. Background Discussion

Hemorrhoids are swollen, often painful veins in the lower portion of the rectum or anus. It is a relatively common disease, the symptoms of which can include anal itching and/or aches and pains, particularly when sitting, blood in the stool, pain during bowel movements, and/or hard or tender lumps near the anus. Hemorrhoids are caused by increased pressure in the veins around the anus, which can occur as a result of pregnancy or childbirth, prolonged constipation, long periods of sitting, infections or the like.

Three to four different stages of hemorrhoid occurrence are known, with various stages of treatment depending on the severity. For the less severe cases, corticosteroid creams or lidocaine creams can reduce pain and/or swelling. For more severe cases that do not respond to topical treatments, various heat treatments can be attempted the objective of which is to shrink the hemorrhoids. For severe cases surgical intervention may be necessary.

Known surgical techniques for treating severe hemorrhoids include hermorrhoidectomy, which involves surgically removing the hemorrhoid, and rubber band ligation techniques. Rubber band ligation involves grasping the bulging hemorrhoid with a suitable surgical instrument, and placing a rubber band or the like around the base of the hemorrhoid. The rubber band strangulates the hemorrhoid knot and cuts off the blood supply. After a period of about 7 days, the hemorrhoid shrivels and dies, and falls off along with the rubber band. Scar tissue forms that continues to hold the veins in place, preventing future bulging.

A significant disadvantage of the rubber band ligation devices and techniques currently on the market is the risk of severe bleeding, which can be fatal. Severe bleeding can occur if the rubber band slips off the hemorrhoid too early (i.e., within the first 7 days). In these instances, postoperative pain and acute bleeding causes a sphincter spasm. Blood will then fill the rectum, or with mild bleeding the colon descendens. When the ampulla recti is filled with a certain amount of blood the patient feels the urge for defecation. A blood loss of up to one liter (20% blood loss) is possible. The consequences of bleeding can be severe and fatal, since often the bleeding will occur while the patient is at home and does not otherwise notice the blood loss until it reaches a critical level and causes hypovolaemic shock.

Thus, there is a need for an improved device and method for surgical ligation of hemorrhoids that reduces the risk that bleeding will occur.

SUMMARY OF THE INVENTION

The present invention provides a ligation device for ligating diseased tissue including a flexible, substantially tubular sleeve adapted to be positioned around tissue to be ligated and having a first end and a second end, and at least one anchoring member coupled to the tubular sleeve. The at least one anchoring member has an anchoring element positioned substantially adjacent to the first end of the sleeve, and the anchoring member has at least one projecting element extending therefrom and adapted to engage healthy tissue when the ligation device is positioned around the tissue to be ligated. The device further includes an elastic element positioned around the periphery of the sleeve and adapted to apply a constrictive force around the periphery of said sleeve.

In one embodiment, the at least one anchoring member further includes a band retaining element, and the elastic element is positioned within the band retaining element. The band retaining element may be a recess, and the at least one anchoring member may be made of an absorbable material such as poliglecaprone 25, poly-p-dioxanone, poly lactid or any combination thereof.

In yet another embodiment, the tubular sleeve is made of a biocompatible mesh, which may be absorbable or non-absorbable, or a film which may be absorbable or non-absorbable.

The at least one projection may extend outwardly or inwardly from the tubular sleeve.

In alternate embodiments, the ligations device may have at least two, or at least four anchoring members.

The tissue to be ligated may be a hemorrhoid.

The present invention also provides a method for placing a ligation device on tissue to be ligated, including the steps of providing a ligation device as described above, providing an implant delivery device including a hollow, tubular device receiving assembly, which has a housing and a slidable collar slidable relative to and over the housing. The housing has a distal end dimensioned to receive therein the tubular sleeve of the ligation device, and the implant delivery device is coupled to a vacuum source. The method further includes inserting the ligation device into the distal end of the housing of the device receiving assembly so that the tubular sleeve of the ligation device is substantially received within the housing, and so that at least a portion of the anchoring member extends outwardly or inwardly from the housing, placing the ligation device in proximity to the tissue to be ligated, applying a vacuum through the implant delivery device so as to draw the tissue to be ligated into the delivery device, and sliding the slidable collar toward the distal end of the delivery device to thereby engage the anchoring member to push the ligation device off the end of the delivery device to thereby deploy the delivery device over the tissue to be ligated.

Also provided is a ligation device for ligating diseased tissue including a flexible, substantially tubular sleeve adapted to be positioned around tissue to be ligated and having a first end and a second end, a plurality of anchoring members coupled to and spaced apart around a periphery of the tubular sleeve, the plurality of anchoring members each having at least one anchoring element positioned substantially adjacent to the first end of the sleeve, and each having a recess therein. The anchoring members have at least one projecting element adapted to engage healthy tissue when the ligation device is positioned around the tissue to be ligated. The device further includes an elastic element positioned around the periphery of the sleeve and within the recesses of the plurality of anchoring members, and adapted to apply a constrictive force around the periphery of the sleeve.

The ligation device may further include at least one capture element projecting over said recess.

These and other features and advantages of the present invention will become apparent from the following more detailed description, when taken in conjunction with the accompanying drawings which illustrate, by way of example, the principles of the invention.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Although the present invention is described in detail in the context of hemorrhoids, the device and methods described herein have application to other surgical conditions for which it is desired to ligate a tissue bundle. For example, the devices and methods described herein may be used to control upper gastric bleeding (e.g., esophageal varicosis, gastric polyposis) or lower GI bleeding due to colonic polyp bleeding or angio dyplasia.

Figure 1A:
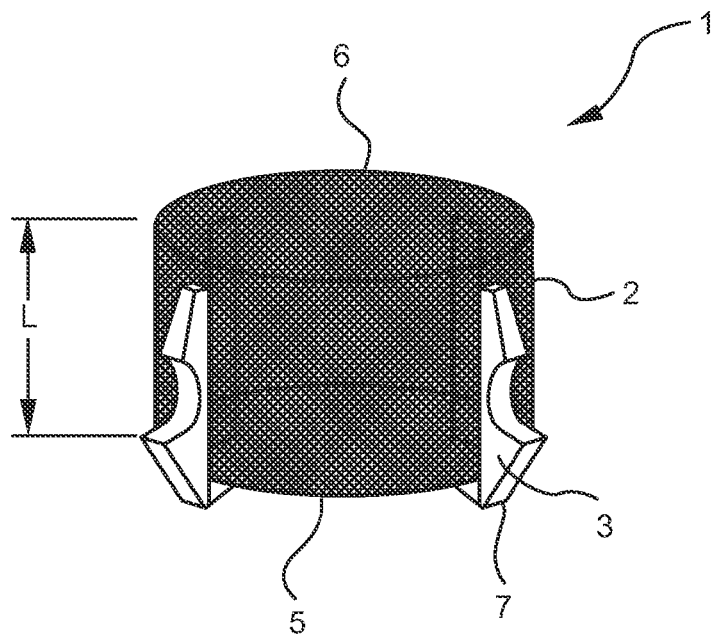
FIGS. 1a and 1b illustrate embodiments of a ligation device according to the present invention.
Figure 1B:
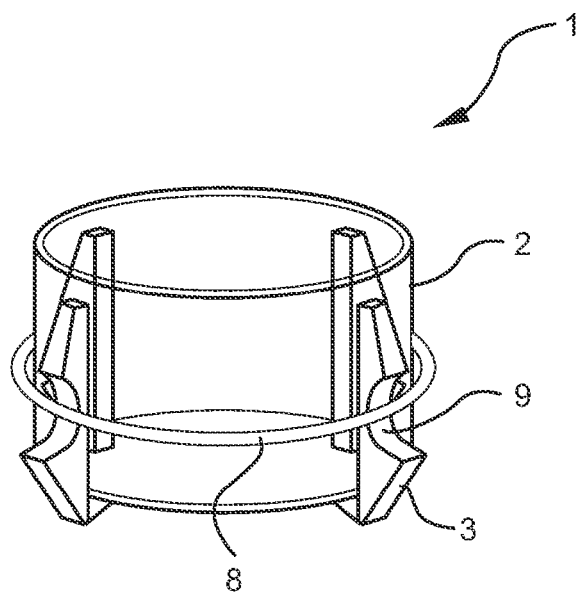

FIG. 1 illustrates a ligation device 1 according to the present invention. The ligation device includes a collapsible sleeve 2 and one or more anchoring members 3 positioned around the periphery of the collapsible sleeve. The collapsible sleeve is substantially tubular having a length L extending between a first end 5 and a second end 6, and is comprised of a biocompatible material, which may be absorbable or non-absorbable. In preferred embodiments, the collapsible sleeve is either a mesh (as shown in FIG. 1a) or a film (as shown in FIG. 1b).

Exemplary mesh materials include PROLENE®, which is a knitted or woven polypropylene mesh having a thickness of approximately 0.7 mm, and which is manufactured by Ethicon, Inc. of Somerville, N.J. Other suitable materials include non-absorbable substances such as polyalkenes, polyethylene, fluorinated polyolefins, polytetrafluoroethylene, polyvinylidenefluoride, polyamides, polyurethanes, polyisoprenes, polystryrenes, polysilicones, polycarbonates, polyaryletherketones, polymetacrylates, polyacrylates, aromatic polyesters, polyimides, and copolymers of polymerisable substances thereof. Further, suitable absorbable materials include polyhydroxy acids, polylactides, polyglycolides, polyhydroybutyrates, polyhydroxyvaleriates, polycaprolactones, polydioxanones, synthetic and natural oligo- and polyaminoacids, polyphosphazenes, polyanhydrides, polyorthoesters, polyphosphates, polyphosphonates, polyalcohols, polysaccharides, polyethers, resorbable glasses, and copolymers of polymerisable substances thereof. Other textile technologies incorporating non-woven techniques may also be suitable.

Another suitable material is created by assembling material or components of a product sold under the name ETHISORB® Dura Patch (sold by Codman & Shurtleff, Inc. of Raynham, Mass.), which is mainly a VICRYL® polyglactin synthetic surgical composite material that is used for tissue reinforcement surgery. VICRYL® is a material that is also manufactured by Ethicon, Inc. ETHISORB®Dura Patch includes a fleece made from VICRYL® (polyglactin 910) and PDS (poly p-dioxanone) undyed yarn which is sandwiched on one side with a piece of dyed poly-p-dioxanone film Suitable film materials include an absorbable material such as Monocryl® poliglecaprone 25 or PDS®, dyed or undyed poly-p-dioxanone film, or non-absorbable materials such as an elastomer.

The collapsible sleeve 2 preferably has a thickness of between 30 µm to 500 µm, more preferably 100 µm, a width of between 3-5 mm, more preferably 4 mm, and a length of between 3-5 cm, more preferably 3 cm.

Figure 2A:
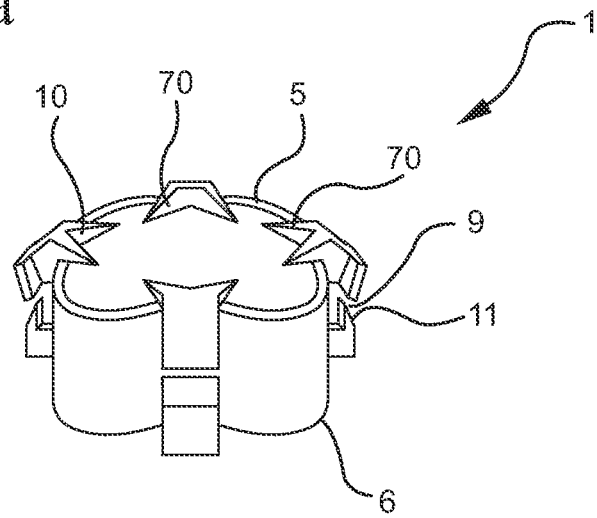
FIGS. 2a and 2b illustrate bottom and top views of an alternate embodiment of a ligation device according to the present invention.
Figure 2B:
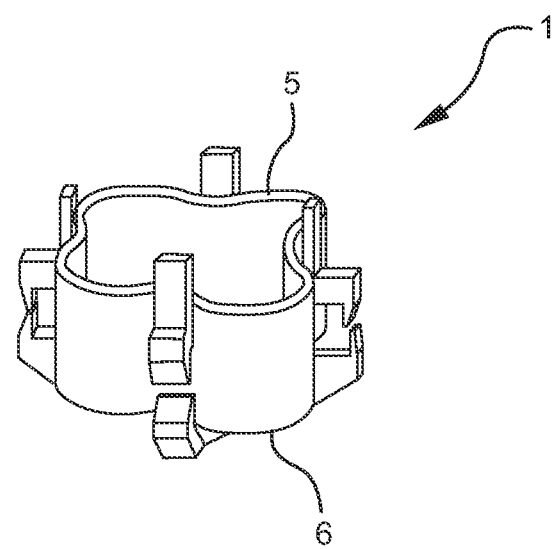
Figure 3:
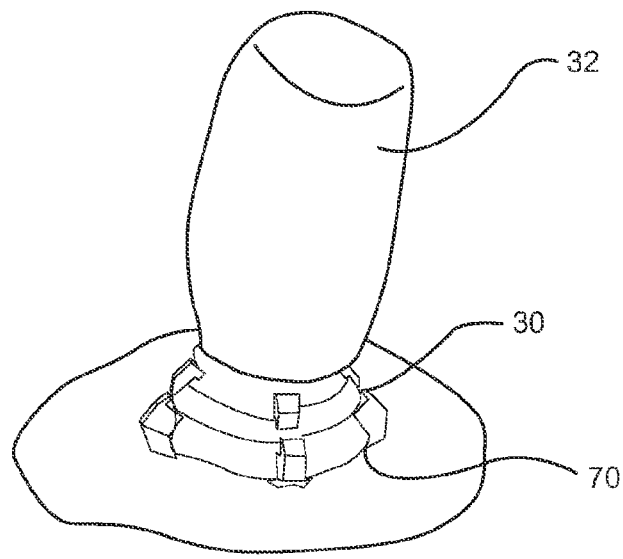
FIG. 3 illustrates a ligation device according to the present invention deployed over a hemorrhoid.

As stated, the ligation device includes one or more anchoring members 3 positioned around the periphery of the collapsible sleeve. In a preferred embodiment, there are at least two such anchoring members. The anchoring member(s) extend along at least a portion of the length L of the collapsible sleeve, but may extend along the entire length as shown in FIGS. 2a and 2b. Each anchoring member has at least one anchoring element 10 at a first end 7 thereof that is positioned at or near the first end 5 of the collapsible sleeve. The anchoring element is a hook, projection or the like, or any design suitable for engaging tissue to secure the ligation device thereto. In the exemplary embodiment shown in FIG. 2a, the anchoring element includes one or more projections 70 that extend inwardly. Although FIG. 2a illustrates the projections extending inwardly into the collapsible sleeve, these projections may alternatively extend outwardly from the collapsible sleeve. The anchoring member is positioned at the first end 5 of the ligation device so that it is designed to engage healthy tissue 30 at the base of the hemorrhoid 32 as shown in FIG. 3. By anchoring into tissue, and in particular healthy tissue, the ligation device of the present invention substantially reduces the risk that the ligation device will prematurely fall off, and that resulting bleeding will occur.

As a further means to prevent the anchoring device of the present invention from prematurely falling off, the anchoring members also include a band retaining element 9, along the length thereof. The band retaining element may be a recess as shown in FIGS. 1a and 1b, and may further be defined by one or more capture elements 11 extending over such a recess as shown in FIGS. 2a and 2b. The recess provides a seat within which the elastic band 8 rests (see FIG. 1b) when the ligation device is fully deployed around a hemorrhoid, ensuring that the elastic band does not slip off the ligation device, and cause the ligation device itself to slip off the hemorrhoid.

Figure 4:
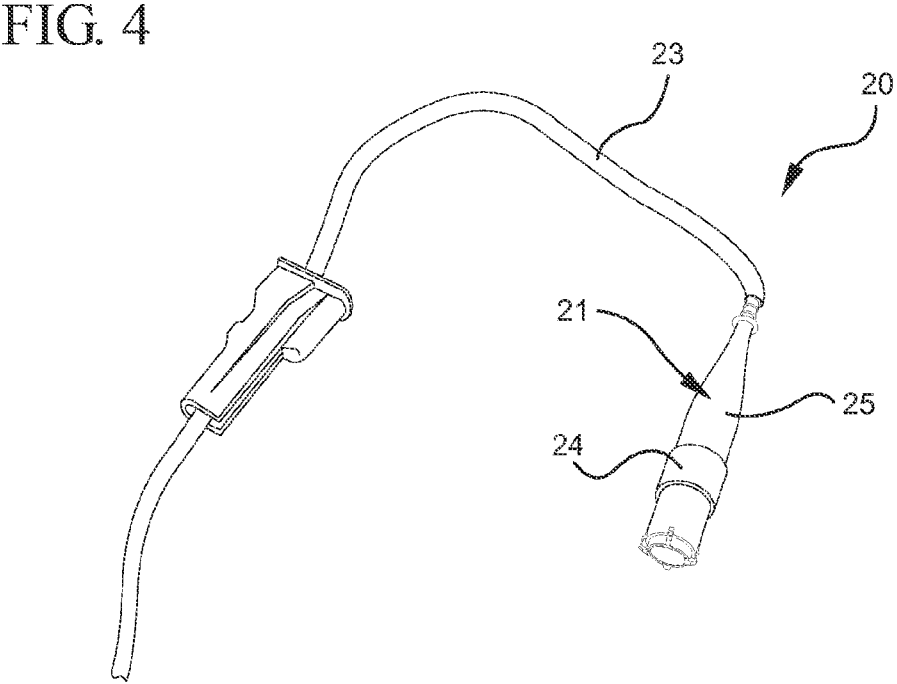
FIG. 4 illustrates an exemplary delivery device loaded with a ligation device according to the present invention.
Figure 5A:
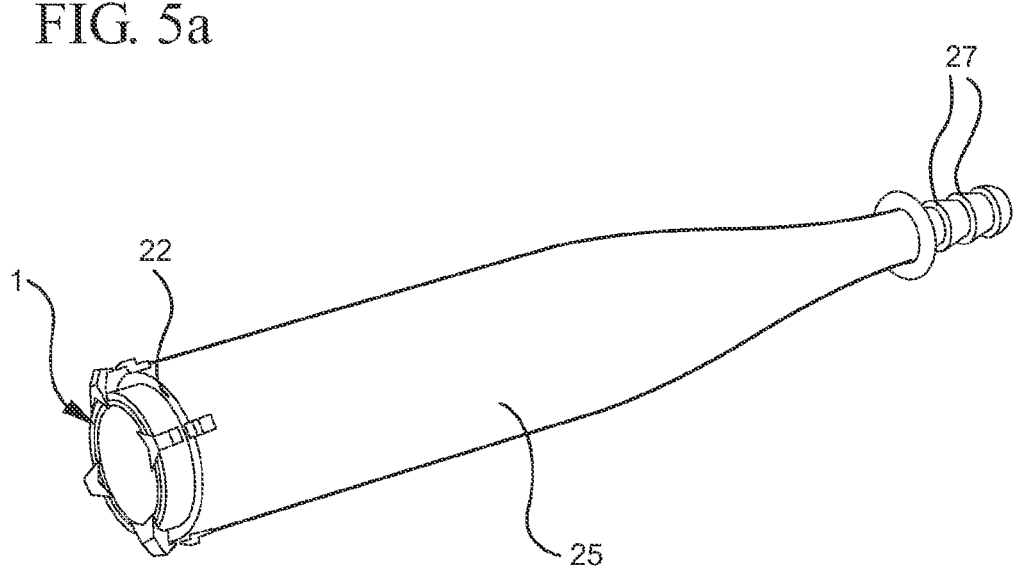
FIGS. 5a and 5b illustrate in greater detail the ligation device receiving portion of the delivery device of FIG. 4 before and after the elastic band element is coupled thereto.
Figure 5B:
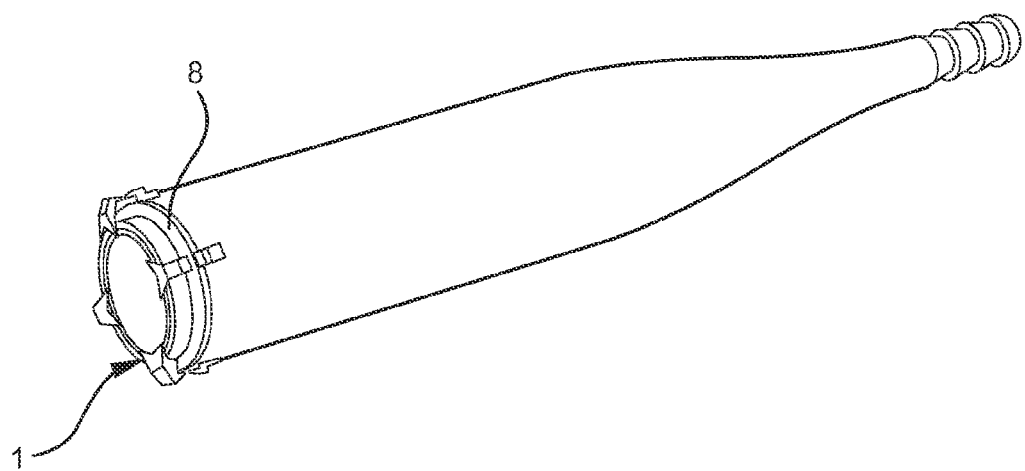
Figure 6:
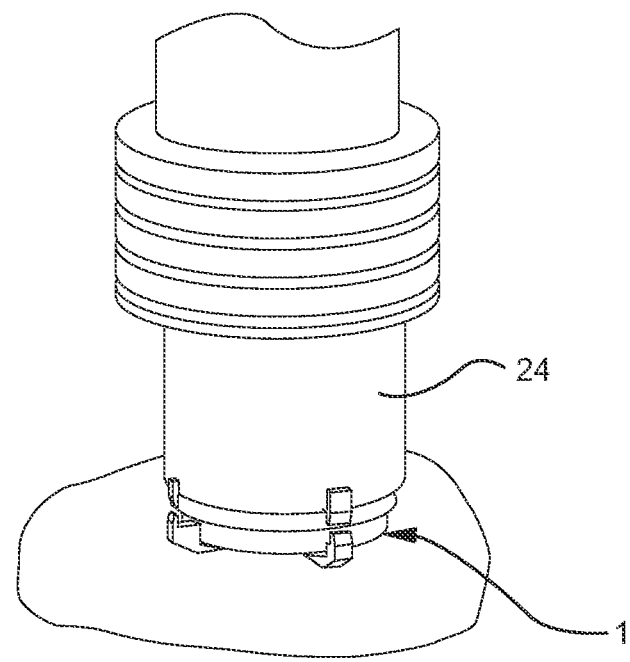
FIG. 6 is an enlarged view of the slidable collar of the delivery device of FIG. 4.

Referring now to FIGS. 4-6, an implant delivery device 20 for applying the ligation devices described above will now be described in detail. The implant delivery device includes a device receiving assembly 21 that receives in a distal end thereof 22 the ligation device 1. The device receiving assembly is a hollow tubular member having an enlarged distal end sized and shaped to receive therein the ligation device as shown. The device receiving assembly is coupled to a vacuum tube 23 that is in turn coupled to a vacuum source (not shown) that applies a vacuum to pull the hemorrhoid through the tubular ligation device to enable the ligation device to be applied over the hemorrhoid as shown in FIG. 3.

The delivery device further includes a slidable collar 24 that is slidable over the housing 25 of the device receiving assembly to push the ligation device off the end of the housing to thereby fully deploy the device over the hemorrhoid. To do so the slidable collar 24 engages the anchor member(s) to push the ligation device off the distal end of the delivery device at the appropriate time. In particular, to apply the ligation device 1, the combination collapsible sleeve and anchoring members 3 are loaded into the end of the housing 25 of the device receiving assembly 21 as described above.

The elastic band 8 is then placed over the proximal end 27 of the housing 25 as shown in FIG. 5a, and moved up along the housing until it passes over the distal end 22 and into place over the ligation device 1 as shown in FIG. 5b. The slidable collar 24 is then placed over the housing 25 from the proximal end until positioned as shown in FIG. 4, and the vacuum tube connected 23 to the proximal end as also shown in FIG. 4. The receiving assembly is then placed over the hemorrhoid knot and suction applied to draw the hemorrhoid knot into the open distal end 22. The slidable collar 24 is then moved toward the distal end of the device receiving assembly 21 until it engages the ligation device as shown in FIG. 6, and pushes it off the distal end 22 and over the hemorrhoid knot. Suction is discontinued and the device receiving assembly withdrawn, thereby leaving the ligation device in place over the hemorrhoid knot as shown in FIG. 3.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. An implantable ligation device adapted to be implanted in a patient for ligating diseased tissue comprising:
    a flexible, substantially tubular sleeve having a first open, unobstructed wend and a second open, unobstructed end and a conduit therethrough extending along a first axis, and adapted to be permanently implanted around tissue to be ligated;
    a plurality of anchoring members fixedly coupled to the tubular sleeve and spaced apart around an exterior periphery of said tubular sleeve with each anchoring member extending along an axis substantially parallel to the first axis and having an outwardly facing recess therein, said plurality of anchoring members each having an anchoring element positioned substantially adjacent to the first end of the sleeve, wherein the anchoring member has at least one projecting element extending therefrom and adapted to engage healthy tissue when the ligation device is positioned around said tissue to be ligated; and
    an elastic element positioned around the periphery of the sleeve and plurality of anchoring members and within the recesses in the anchoring members, and adapted to apply a constrictive force around said periphery of said sleeve when implanted in the body to thereby secure said ligation device around said diseased tissue.

2. The ligation device according to claim 1, wherein the at least one projection extends outwardly from the tubular sleeve.

3. The ligation device according to claim 1, wherein the at least one projection extends inwardly into the tubular sleeve.

4. The ligation device according to claim 1, wherein the ligation device has at least four anchoring members.

5. The ligation device according to claim 1, wherein the tissue to be ligated is a hemorrhoid.

6. The ligation device according to claim 1, wherein at least one of the anchoring members further comprises at least one capture element projecting over said recess.

7. The ligation device according to claim 1, wherein the plurality of anchoring members are comprised of an absorbable material.

8. The ligation device according to claim 7, wherein the absorbable material is selected from the group consisting of poliglecaprone 25, poly-p-dioxanone, poly lactid and combinations thereof.

9. The ligation device according to claim 1, wherein the tubular sleeve is comprised of a biocompatible mesh.

10. The ligation device according to claim 6, wherein the mesh is comprised of a non-absorbable material selected from the group consisting of polyalkenes, polyethylene, fluorinated polyolefins, polytetrafluoroethylene, polyvinylidenefluoride, polyamides, polyurethanes, polyisoprenes, polystryrenes, polysilicones, polycarbonates, polyaryletherketones, polymetacrylates, polyacrylates, aromatic polyesters, polyimides, and copolymers of polymerisable substances thereof; or an absorbable material selected from the group consisting of polyhydroxy acids, polylactides, polyglycolides, polyhydroybutyrates, polyhydroxyvaleriates, polycaprolactones, polydioxanones, synthetic and natural oligo- and polyaminoacids, polyphosphazenes, polyanhydrides, polyorthoesters, polyphosphates, polyphosphonates, polyalcohols, polysaccharides, polyethers, resorbable glasses, and copolymers of polymerisable substances thereof.

11. The ligation device according to claim 1, wherein the tubular sleeve is comprised of a biocompatible film.

12. The ligation device according to claim 11, wherein the film is comprised of an absorbable material.

13. A method for placing a ligation device on tissue to be ligated, comprising
    providing a ligation device as set forth in claim 1;
    providing an implant delivery device including a hollow, tubular device receiving assembly, the device receiving assembly including a housing and a slidable collar slidable relative to and over the housing, and the housing of the device receiving assembly having a distal end dimensioned to receive therein the tubular sleeve of the ligation device, the implant delivery device being coupled to a vacuum source;
    inserting the ligation device into the distal end of the housing of the device receiving assembly so that the tubular sleeve of the ligation device is substantially received within the housing, and so that at least a portion of the anchoring member extends outwardly or inwardly from the housing;
    placing the ligation device in proximity to the tissue to be ligated;
    applying a vacuum through the implant delivery device so as to draw the tissue to be ligated into the delivery device;
    sliding the slidable collar toward the distal end of the delivery device to thereby engage the anchoring member to push the ligation device off the end of the delivery device to thereby deploy the delivery device over the tissue to be ligated.

* * * * *